United States Patent [19]

Parrinello et al.

[11] Patent Number: 5,166,383
[45] Date of Patent: Nov. 24, 1992

[54] ORGANOSILANE AMINALS AND AMINAL ADDUCTS

[75] Inventors: Giovanni Parrinello, Duisburg, Belgium; Hubert Simon, Mulhouse, France; Rolf Mülhaupt, Freiburg, Fed. Rep. of Germany

[73] Assignee: Ciba-Geigy Corporation, Ardsley, N.Y.

[21] Appl. No.: 534,782

[22] Filed: Jun. 7, 1990

[30] Foreign Application Priority Data

Jun. 13, 1989 [CH] Switzerland .......................... 2203/89

[51] Int. Cl.$^5$ .................................................. C07F 7/10
[52] U.S. Cl. .................................... 556/414; 556/419; 556/420; 556/421
[58] Field of Search .................... 564/23, 44, 59; 556/420, 421, 414, 419

[56] References Cited

U.S. PATENT DOCUMENTS

| | | | |
|---|---|---|---|
| 3,787,416 | 1/1974 | Cyba | 544/335 |
| 4,082,689 | 4/1978 | Heyden et al. | 564/59 |
| 4,289,869 | 9/1981 | Zengel et al. | 528/73 |
| 4,404,379 | 9/1983 | Hajek et al. | 544/231 |

FOREIGN PATENT DOCUMENTS 3414877 10/1985 Fed. Rep. of Germany .

OTHER PUBLICATIONS

Abst. for DE 3,414,877 (85-270859/44), 1985.

*Primary Examiner*—Mukund J. Shah
*Assistant Examiner*—Y. N. Gupta
*Attorney, Agent, or Firm*—JoAnn Villamizar

[57] ABSTRACT

Compounds of general formula I

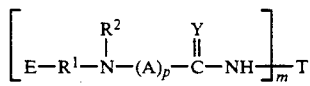

wherein
$R^2$ is hydrogen unsubstituted $C_1$-$C_6$alkyl or $C_1$-$C_6$alkyl substituted by —OH, —CN or by —Si(OR$^3$)$_{3-q}$R$^4_q$, or $C_2$-$C_6$alkenyl,
$R^3$ is $C_1$-$C_4$alkyl, or two radicals $R^3$ together are $C_1$-$C_4$alkylene,
$R^4$ is $C_1$-$C_4$alkyl or phenyl, and
q is from 0 to 2, and
E is a radical of the formula

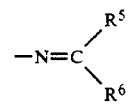

wherein
$R^5$ is hydrogen or $C_1$-$C_4$alkyl and
$R^6$ is hydrogen, or
$R^5$ and $R^6$ together are $C_4$-$C_8$alkylene, or
and
A is $+(CH_2)_r$—O$+$, wherein r is 1,2 or 3, and p is 0 or 1, and
Y is oxygen or sulfur; and
wherein
T is a radical —R$^9$—Si(OR$^3$)$_{3-q}$R$^4_q$, a radical of the formula

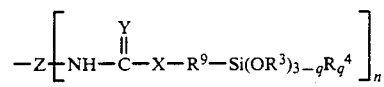

X is —S— or —NH—, and
Z is an organic radical derived from a polyisocyanate or polyisothiocyanate having at least 2 NCO or NCS groups, respectively,
are suitable as adhesion promoters, especially for moisture-curing polyurethane resins.

16 Claims, No Drawings

ORGANOSILANE AMINALS AND AMINAL ADDUCTS

The present invention relates to nitrogen-containing silanes, to their use as adhesion promoters, and to 1- or 2-component polyurethane resins that contain those adhesion promoters and are used as adhesives, sealing compounds, surface coatings or insulating materials.

The adhesion of cured polyurethanes to glass or metal is unsatisfactory in many technical applications, which has led to the use of primers. These produce a good bond between polyurethane and glass or metal, which is little impaired even by high moisture levels, elevated temperatures and high mechanical loads. As primers there have proved suitable, for example, aminoalkylalkoxysilanes (see Plueddemann et al. "Silane coupling agents", Plenum Press, N.Y. [1982]). However, the most effective aminosilane adhesion promoters cannot be used in unmodified form as built-in adhesion promoters in moisture-curing polyurethanes, since the amino groups react with isocyanate groups. DE-OS 3,414,877, therefore, describes ketimines and aldimines of aminoalkylsilanes which can be added to polyurethane adhesives without impairing their stability to storage.

Furthermore, U.S. Pat. Nos. 3,787,416 and 4,289,869 describe cyclic aminals as curing agents for polyurethane resins. U.S. Pat. No. 4,404,379 discloses reaction products of cyclic aminals with isocyanates to give adducts which are suitable as curing agents for polyurethane resins. However, those aminals and aminal adducts do not contain silane-containing groups.

A class of compounds has now been found which are added to 1- or 2-component polyurethane resin adhesives, sealing compounds, lacquers and insulating materials and produce a significant increase in the adhesion to glass, metal, lacquered steel and plastics, while the rate of curing is not impaired or is even increased.

The present invention relates to compounds of general formula I

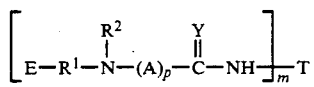  I wherein
$R^1$ is $C_2$–$C_3$alkylene,
$R^2$ is hydrogen, unsubstituted $C_1$–$C_6$alkyl or $C_1$–$C_6$alkyl substituted by —OH, —CN or by —Si(OR$^3$)$_{3-q}$R$^4_q$, or $C_2$–$C_6$alkenyl,
$R^3$ is $C_1$–$C_4$alkyl, or two radicals $R^3$ together are $C_1$–$C_4$alkylene,
$R^4$ is $C_1$–$C_4$alkyl or phenyl, and
q is from 0 to 2, and
E is a radical of the formula

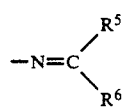

wherein
$R^5$ is hydrogen or $C_1$–$C_4$alkyl and
$R^6$ is hydrogen, or
$R^5$ and $R^6$ together are $C_4$–$C_8$alkylene, or
E together with $R^2$ is a radical of the formula

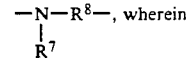, wherein $R^7$ is hydrogen, $C_1$–$C_4$alkyl or —R$^9$—Si(OR$^3$)$_{3-q}$R$^4_q$, wherein $R^3$, $R^4$ and q are as defined above and
$R^9$ is $C_1$–$C_8$alkylene, and
$R^8$ is a radical

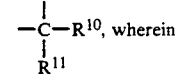, wherein $R^{10}$ is hydrogen or $C_1$–$C_4$alkyl and
$R^{11}$ is hydrogen, or
$R^{10}$ and $R^{11}$ together are $C_4$–$C_8$alkylene, and
A is —(CH$_2$)$_r$—O—, wherein r is 1, 2 or 3, and p is 0 or 1, and
Y is oxygen or sulfur; and
wherein
T is a radical —R$^9$—Si(OR$^3$)$_{3-q}$R$^4_q$, a radical of the formula

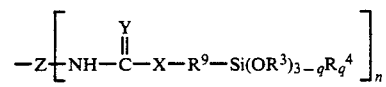

or, when $R^7$ is a radical of the formula —R$^9$—Si(OR$^3$)$_{3-q}$R$^4_q$ and m is $\geq 2$, T is an m-valent radical Z, wherein $R^3$, $R^4$, $R^9$, Y and q are as defined above,
X is —S— or —NH—, and
Z is an organic radical derived from a polyisocyanate or polyisothiocyanate having at least 2 NCO or NCS groups, respectively,
and
m is $\geq 1$, and
n is $\geq 1$.

Preferably, $R^{10}$ is $C_1$–$C_4$alkyl.
When $R^3$, $R^4$, $R^5$, $R^7$ and $R^{10}$ are $C_1$–$C_4$alkyl or when $R^2$ is $C_1$–$C_6$alkyl, alkyl is, for example, methyl, ethyl, n-propyl, isopropyl, n-butyl, isobutyl and tert.-butyl, and in the case of $R^2$ also n-pentyl or n-hexyl.

The preferred meaning of $R^3$ and $R^4$ as alkyl is methyl and ethyl, especially methyl.

When $R^1$ is $C_2$–$C_3$alkylene, $R^3$ is $C_1$–$C_4$alkylene, $R^5$ together with $R^6$ or $R^{10}$ together with $R^{11}$ is $C_4$–$C_8$alkylene and $R^9$ is $C_1$–$C_8$alkylene, alkylene is straight-chained or branched alkylene, straight-chained alkylene being preferred. Examples are, for $R^3$ and $R^9$, methylene, ethylene, propylene, trimethylene, tetramethylene and 2-methyl-1,3-trimethylene, and for $R^9$ additionally and also for $R^5$/$R^6$ and $R^{10}$/$R^{11}$ pentamethylene, 2-methyl-1,4-tetramethylene, 3-propyl-1,3-trimethylene, 1,6-hexamethylene, 1,7-heptamethylene, 1,8-octamethylene and 2-ethyl-1,2-hexamethylene, the meaning of $R^1$ being restricted to ethylene, propylene and trimethylene.

Preferably, $R^3$ is ethylene, $R^5$/$R^6$ and $R^{10}$/$R^{11}$ are tetramethylene and pentamethylene and $R^9$ is $C_1$–$C_4$alkylene, especially trimethylene or ethylene.

When $R^2$ is $C_2$–$C_6$alkenyl, it is straight-chained or branched alkenyl, preferably straight-chained alkenyl, that contains one or more double bonds, but preferably one double bond, such as, for example, vinyl, allyl, n-butenyl, 1,3-butadienyl, isopentenyl, n-pentenyl or n-hexenyl.

When $R^2$ as $C_1$–$C_6$alkyl is substituted by OH, CN or $Si(OR^3)_{3-q}R^4_q$ groups, it may be mono- or poly-substituted, preferably mono-substituted. The substitution may be in any possible position, but the terminal position is preferred.

When E is a radical of the formula

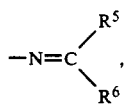

$R^2$ is preferably $C_1$–$C_4$alkyl, especially methyl.

The parameter p in formula I is preferably 0.

Likewise, the parameter q is preferably 0.

The radical Z is derived from a polyisocyanate or polyisothiocyanate having at least 2 NCO or NCS groups, respectively. The NCO or NCS functionality $\geq 2$ of the polyisocyanate or polyisothiocyanate according to the invention is achieved, for example, by converting polyamines, such as, for example, amino-terminated polyether polyols, into polyisocyanates or polyisothiocyanates having a functionality $\geq 2$ by means of phosgenation or thiophosgenation, respectively. The polyisocyanates or polyisothiocyanates obtainable in this manner can either be used directly or can first be reacted with diols, polyols, dimercaptans, diamines or polyamines to form NCO- or NCS-terminated prepolymers. The polyisocyanates obtainable as described below may also be reacted in the same manner.

A further possible method of preparing polyisocyanates having an NCO functionality $\geq 2$ is the oligomerisation of diisocyanates. For example, diisocyanates, e.g. hexamethylene-diisocyanate, can be converted by means of partial hydrolysis into products containing biuret groups (such as, for example, the Bayer product Desmodur ® N100).

Furthermore, diisocyanates, such as, for example, hexamethylene-diisocyanate, can be partially trimerised so as to produce higher-functional polyisocyanates that contain isocyanurate rings, such as, for example, the Bayer product Desmodur ® N3200.

Chain-lengthening by reaction of diisocyanates with polyfunctional H-acidic compounds having a functionality $\geq 2$, such as, for example, triols, tetrols, pentols, triamines, polyamines and polymercaptans, also gives rise to polyisocyanates having an NCO functionality $\geq 2$, in which case the NCO/OH ratio is $>1$, but preferably $>3:1$, especially $>10:1$.

Suitable diisocyanates are both aromatic and aliphatic, heterocyclic, monocyclic and polycyclic, bifunctional isocyanate compounds. Examples of such compounds are toluylene-diisocyanate, diphenylmethane-diisocyanate, naphthylene-diisocyanate, xylylene-diisocyanate, hexamethylene-diisocyanate, trimethylhexamethylene-diisocyanate, isophorone-diisocyanate and dicyclohexylmethane-diisocyanate.

The parameters m and n are each independently of the other from 1 to 49, preferably from 1 to 9, especially from 1 to 5, and more especially 1, 2 and 3. The sum of n+m is generally from 2 to 50, preferably from 2 to 10, especially from 2 to 6.

The radical Z preferably has a mean molecular weight Mn<10,000, especially Mn<4,000.

Y is preferably O.

Preferred compounds are those of formula I wherein Z is derived from an aliphatic, cycloaliphatic, aliphatic-/aromatic, aromatic or heterocyclic polyisocyanate or polyisothiocyanate having $\geq 2$ NCO or NCS groups, this radical Z optionally containing one or more ester, ether, urethane, thiourethane, isocyanurate, urea or biuret functions.

Especially preferred compounds are those of formula I wherein Z is derived from an aliphatic or mixed aliphatic/aromatic polyisocyanate having $\geq 2$ NCO groups, this radical Z optionally containing a total of one or two ester, ether, urethane, thiourethane, isocyanurate, urea or biuret functions.

If Z in the compounds of formula I contains ether oxygens, they may be monoethers or oligoethers, such as, for example, a group of the formula $-CH[CH_3]-CH_2-O)_{\overline{y}}$ or $(CH_2CH_2CH_2CH_2-O)_{\overline{y}}$ wherein y is a number from 1 to 80, preferably from 1 to 20.

If the radical Z in the compounds of formula I contains carbamate or thiocarbamate groups, those groups are derivatives obtainable by reaction of polyols with compounds containing isocyanate or isothiocyanate groups, respectively. They are also to be understood as being radicals that contain both one or more urethane groups and one or more thiourethane groups, for example groups that contain a bridge member of the formula

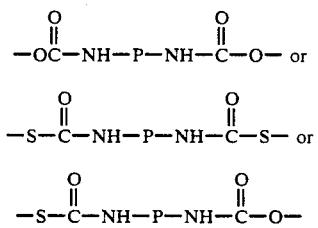

wherein P is the radical of the polyol.

OH-terminated polyethers or polyesters, for example, may also be used as polyols.

In preferred compounds of formula I, the radical Z contains two ester, carbamate, isocyanurate, urea or biuret functions, and in especially preferred compounds it contains one ester, carbamate, isocyanurate, urea or biuret function. The ether functions are an exception in this respect since, as indicated above, they are capable of forming oligoether bridge members. Such compounds may therefore contain up to 80, preferably up to 20, ether functions.

Preferred compounds of formula I are those wherein E together with $R^2$ is a radical of the formula

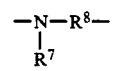

and $R^1$ is ethylene.

Also preferred are compounds of formula I wherein E is a radical of the formula

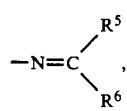

especially those wherein $R^5$ is isopropyl or tert.-butyl or $R^5$ together with $R^6$ is tetramethylene or pentamethylene.

A further preferred embodiment relates to compounds of formula I wherein T is a radical of the formula

$$-R^9-Si(OR^3)_{3-q}R^4_q \text{ or}$$

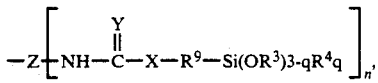

especially those wherein at least one radical X is —S—.

Especially preferred are compounds of formula I wherein p is 0 and m is 1, E is a radical

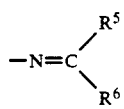

wherein $R^5$ is $C_3$- or $C_4$-alkyl and $R^2$ is $C_1$-$C_4$alkyl.

The preparation of the compounds of formula I is effected in a manner known per se and can be illustrated most simply with reference to the following reaction schemes.

I. Aminal or imine-amine part $$\underset{(A)}{HN\!-\!R^1\!-\!NH_2} + \underset{(B)}{R^{10}\!-\!C(O)\!-\!R^{11}} \longrightarrow$$

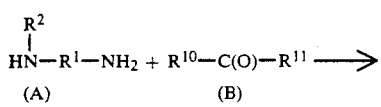

This method is carried out, for example, in the manner described in U.S. Pat. No. 4,404,379. The educts (A) and (B) are known compounds, some of which are commercially available, or they can be prepared in a simple, known manner. 3-Methylaminopropylamine and 3-(2-aminoethylamino)propyltrimethoxysilane are especially suitable as educts (A). Suitable educts (B) are, for example, the carbonyl compounds formaldehyde, acetaldehyde, propionaldehyde, butyraldehyde, isobutyraldehyde, pivalaldehyde, cyclopentanone and cyclohexanone.

By reacting (C) with compounds containing reactive double bonds, such as, for example, acrylonitrile, in accordance with the method described in EP-A 70536, it is possible to prepare aminals of formula (E), wherein the radicals $R^2$, independently of one another, may have different meanings.

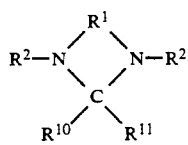

The aminals (C) and (E) and the imine-amines (D) so prepared can be reacted in a further step with a polyisocyanate $Z\!-\!(NCO)\geq 2$ or polyisothiocyanate $Z\!-\!(NCS)\geq 2$.

II. Silane part

The amino- or mercapto-alkoxysilanes used in accordance with the invention are known compounds. Some of them are commercially available, or they can be prepared by known methods. Compounds of this type are described in detail in "Silane Coupling Agents" by E. P. Plueddemann, Plenum Press, New York, 1982.

III. Polyisocyanate $Z\!-\!(NCO)\geq 2$ or polyisothiocyanate $Z\!-\!(NCS)\geq 2$ These components are prepared by methods known in the literature, such as are described, for example, in U.S. Pat. No. 3,492,330; GB-PS 994,890; DE-PS 1,022,789; DE-PS 1,222,067; DE-PS 1,027,394; DE-OS 1,929,034; DE-OS 2,004,048; U.S. Pat. No. 3,394,164; DE-PS 1,101,394; GB-PS 889,050; BE-PS 723,640; GB-PS 956,474; GB-PS 1,072,956; U.S. Pat. No. 3,567,763 or DE-PS 1,231,688.

The polyisothiocyanates can be prepared analogously. Instead of diisocyanates, the corresponding diisothiocyanates are used as educts. Aliphatic educts can be prepared by the methods described in U.S. Pat. No. 3,787,472 and aromatic educts can be prepared by the method described in "Org. Syntheses"; Collective Volume 1, p. 447, John Wiley, New York (1948).

IV. Reaction of the polyisocyanates or polyisothiocyanates respectively according to III. with the aminals (C) and/or (E) or the imine-amines (D) and with the silanes according to II. to give the compounds of formula I The polyisocyanates or polyisothiocyanates can be reacted with the other two components in succession or simultaneously. When the reaction is carried out stepwise, it is possible to react first the aminal compound or imine-amine compound with the polyisocyanate or polyisothiocyanate and then the adduct with the alkoxysilane, or vice versa. It is also possible to add various aminal, imine-amine or silane components to the polyisocyanate or polyisothiocyanate, it being possible to react the various components in turn, that is to say, for example, first adding a silane, then adding an aminal or imine-amine, and finally adding the second silane.

The reaction is generally carried out without a solvent but, if required, one or all component(s) may be diluted by a suitable inert solvent, for example in order to adapt the viscosity to requirements.

The addition itself is carried out at temperatures of from 15° C. to 200° C., but preferably at temperatures of from 30° C. to 140° C.

The course of the reaction can be followed by infrared spectroscopy or titration.

In the addition reactions it is also possible to use catalysts of the type known per se, such as, for example, tertiary amines, e.g. triethylamine, N-methylmorpholine, N,N,N',N'-tetramethylethylenediamine and 1,4-diazabicyclo(2.2.2)octane. Organometal compounds, especially organotin compounds, may also be used as catalysts.

Examples of organotin compounds are tin(II) salts of carboxylic acids, such as, for example, tin(II) acetate, tin(II) octoate and tin(II) laurate, or the dialkyltin salts of carboxylic acids, such as, for example, dibutyltin diacetate, dibutyltin dilaurate or dioctyltin diacetate.

In the addition of the aminal or imine-amine and silane components to the polyisocyanates or polyisothiocyanates, the stoichiometric ratios maintained are such that the ratio of the NH or $NH_2$ groups of the aminals or imine-amines and the $NH_2$ or SH groups of the silanes is approximately equimolar with respect to the NCO or NCS groups of the polyisocyanates or polyisothiocyanates. The adduct may still contain free NCO or NCS groups, but preferably there is no free NCO or NCS group present.

By means of the stoichiometric ratio of the educts in the addition reaction it is possible to control the ratio of aminal or ureaimine radicals to silane radicals in the compounds of formula I according to the invention. For that purpose, the aminal or imine-amine compound and the silane compound are preferably reacted with the polyisocyanate or polyisothiocyanate in separate steps. The first step is generally carried out with a ratio of NH or $NH_2$ groups or SH groups to NCO or NCS groups of less than 1. The preferred aminal-NH or imine-amine-$NH_2$/NCO or NCS ratio is from 1:2 to 1:6, especially from 1:3 to 1:5. The preferred ratio of silane-$NH_2$ or —SH/NCO or NCS groups is from 2:3 to 1:5, especially from 2:3 to 1:2.

In the second step, the remaining free NCO or NCS groups are generally reacted with the aminal-NH or imine-amine-$NH_2$ groups and, as the case may be, silane-$NH_2$ or —SH groups. To that end, the stoichiometric ratio of H-acidic groups to NCO or NCS groups is $\geq 1$, preferably from 4:1 to 1:1, especially from 2:1 to 1:1.

It is also possible, however, to react the remaining free NCO or NCS groups only partially in the second step. In that case, the stoichiometric ratios are the same as those given for the first addition step. It is preferable to adopt such a procedure when two or more different aminal or imine-amine or silane compounds are added.

The compounds according to the invention can be used in polyurethane resins as adhesion promoters. Their use in moisture-curing polyurethane resins which are employed as adhesives, sealing compounds, lacquers or insulating materials is especially effective. In the case of adhesives, the compounds according to the invention have properties that enable them to be used in two-component and, more especially, in one-component systems. When the compounds according to the invention are used as built-in adhesion promoters in the above-mentioned substrates, the surfaces to be bonded need not be pretreated with a primer. Fields of application are, for example, the bonding of windscreens and headlamps in motor vehicle manufacture. Compounds of formula I wherein $m \geq 2$ may also be used as moisture-activated curing agents for the above-mentioned substrates. Furthermore, compounds of formula I may be used as primers for the pretreatment of substrates.

If the substrate is a moisture-curing polyurethane, then it contains as main constituent polyfunctional isocyanates and/or polyurethane prepolymers. Both aromatic and aliphatic, monocyclic and polycyclic, polyfunctional isocyanate compounds are suitable here. For example, in accordance with a first form toluylene-diisocyanate or diphenylmethanediisocyanate may be used as aromatic isocyanate compound. Industrial diphenylmethane-diisocyanate having a content of higher-functional diisocyanates and a functionality with respect to isocyanate groups of more than 2 is especially suitable. A further suitable aliphatic diisocyanate is xylylene-diisocyanate. Furthermore, a large number of aliphatic isocyanates having a functionality of 2 and above can be used. Examples here are isophorone-diisocyanate and dicyclohexylmethane-diisocyanate as cyclic aliphatic diisocyanates. Further examples are aliphatic, straight-chained diisocyanates such as are obtained by phosgenation of diamines, for example tetramethylene-diisocyanate or hexamethylene-diisocyanate.

In accordance with a preferred form of the invention, polyurethane prepolymers are used instead of the polyfunctional isocyanate compounds. Prepolymers should here be understood as being the adducts of an excess of polyfunctional isocyanates with polyfunctional alcohols, for example the reaction products of one of the afore-mentioned aromatic or aliphatic diisocyanates with ethylene glycol, propylene glycol, glycerol, trimethylolpropane or pentaerythritol. It is also possible to use as prepolymers reaction products of diisocyanates with polyether polyols, for example polyether polyols based on polyethylene oxide or based on polypropylene oxide. Polyurethane prepolymers based on polyether polyols having molecular weights of from 200 to 10,000, especially from 500 to 3,000, are preferred. A large number of such polyether polyols is known to the person skilled in the field of polyurethanes; they are available from numerous manufacturers and are characterised by their molecular weight (number average), which can be calculated from end group analyses. Other suitable polyether polyols are polyether polyols based on polytetrahydrofuran.

Instead of polyether polyols it is also possible to use polyester polyols. Suitable polyester polyols are reaction products of polyfunctional acids with polyfunctional alcohols, for example polyesters based on aliphatic and/or aromatic dicarboxylic acids and polyfunctional alcohols having a functionality of from 2 to 4. It is therefore possible to use polyesters of adipic acid, sebacic acid, phthalic acid, hydrophthalic acid and/or trimellitic acid on the one hand and ethylene glycol, propylene glycol, neopentyl glycol, hexane glycol, glycerol and/or trimethylolpropane on the other hand. Polyester polyols having a molecular weight (number average) of from 500 to 5,000, especially from 600 to 2,000, are particularly suitable. Other suitable polyester polyols are the reaction products of caprolactone with alcohols having a functionality of from 2 to 4, for example the addition product of 1 to 5 moles of caprolactone with 1 mole of ethylene glycol, propylene glycol, glycerol and/or trimethylolpropane.

A further suitable class of polyfunctional alcohols is polybutadienols. These are oligomers based on butadiene and containing OH groups as end groups. In this case products having a molecular weight in the range of from 200 to 4,000, especially from 500 to 3,000, are suitable. Also suitable are siloxane prepolymers, preferably in combination with other prepolymers.

In the preparation of the polyurethane prepolymers, the ratio of OH groups of the alcohol component to isocyanate groups is important. It is generally from 1:2 to 1:10. Relatively high excesses of isocyanate tend to produce low-viscosity polyurethane prepolymers, whereas lower isocyanate excesses produce highly viscous preparations, generally only just spreadable with a trowel.

It is known to the person skilled in the field of polyurethanes that the cross-linking density and thus the hardness of the polyurethanes increases with the functionality of the isocyanate component or the polyol. Reference is made here to the general technical literature, for example to the monograph by Saunders and Frisch, "Polyurethanes, Chemistry and Technology", Vol. XVI of the High Polymers series "Interscience Publishers", New York/London, Part I (1962) and Part II (1964).

The polyurethane preparations according to the invention may also contain various adjuvants. For example, fillers may be used. Suitable fillers are inorganic compounds that are non-reactive towards isocyanates, such as, for example, chalk or powdered lime, precipitated and/or pyrogenic silicas, zeolites, bentonites, ground minerals and other inorganic fillers known to the person skilled in that field, especially short-cut fibres etc. For many applications, fillers that impart thixotropy to the preparations are preferred, for example swellable plastics, especially PVC.

In addition to the above-mentioned compounds, the polyurethane preparations according to the invention may contain other adjuvants, for example solvents. Suitable solvents are those which do not themselves react with isocyanate groups, such as, for example, halogenated hydrocarbons, esters, ketones, aromatic hydrocarbons, etc. Plasticisers, flame-proofing agents, retardants, colourings and anti-ageing agents, such as are known in polyurethane adhesives and sealing compounds, may also be incorporated.

For many applications it is desirable to add foam-stabilisers to the polyurethane preparations according to the invention. As foam-stabilisers there may be used so-called silico-surfactants. These are block copolymers which are composed of a polysiloxane block and one or more polyoxyethylene and/or polyoxypropylene blocks. The polyurethane preparations according to the invention may also contain flame-retarding and plasticising additives. Compounds containing phosphorus and/or halogen atoms are customarily used, such as tricresyl phosphate, diphenylcresyl phosphate, tris-2-chloroethyl phosphate, tris-2-chloropropyl phosphate and tris-2,3-dibromopropyl phosphate. In addition, it is also possible to use flame-proofing agents, for example chlorinated paraffins, halophosphides, ammonium phosphate and halogen- and phosphorus-containing resins. For many applications, plasticisers are also of importance as further additives. Examples of suitable plasticisers are esters of phthalic acid or esters of long-chain dicarboxylic acids, for example sebacic acid esters or azelaic acid esters. So-called epoxide plasticisers, for example epoxidised fatty acid derivatives, may also be used.

Other possible additives are basic accelerators. Basic accelerators are, for example, tertiary bases, such as bis-(N,N'-dimethylamino)-diethyl ether, dimethylaminocyclohexane, N,N-dimethylbenzylamine, N-methylmorpholine and also the reaction products of dialkyl-($\beta$-hydroxyethyl)-amine with monoisocyanates and esterification products of dialkyl-($\beta$-hydroxyethyl)-amine and dicarboxylic acids. Another important accelerator is 1,4-diamino-bicyclo-(2.2.2)-octane. Non-basic substances may also be used as accelerators. In this connection there may be mentioned metal compounds, for example iron acetylacetonate and tin(II) 2-ethylhexoate, dibutyltin dilaurate and molybdenum glycolate.

The compounds of formula I are added to polyurethane prepolymers in amounts of from 0.1 to 20% by weight, preferably from 0.5 to 5% by weight, especially from 0.5 to 2.5% by weight, relative to the prepolymer.

When the compounds of formula I are used as curing agents, the molar ratio of liberated

groups to free isocyanate groups in the prepolymer should be from 0.5 to 1.5:1, preferably from 0.9 to 1.1:1.

PREPARATION OF THE STARTING MATERIALS

EXAMPLE A 1-methyl-hexahydropyrimidine

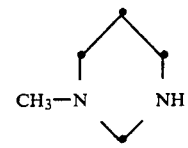

The compound is prepared in the manner described in U.S. Pat. No. 4,404,379. Boiling point: 78° C./266 mbar $^1$H-NMR: $\delta$3.30 (s, N—C$\underline{H}_2$—N); 2.79 (t, J=5.6 Hz, 2H); 2.53 (t, J=5.6 Hz, 2$\overline{H}$); 2.15 (s, C$\underline{H}_3$); 1.63 (p, J=5.6 Hz, 2H).

$^{13}$C-NMR (CDCl$_3$): $\delta$70.3; 54.2; 43.4; 41.7; 26.2.

| C$_5$H$_{12}$N$_2$ | Elemental analysis: | |
|---|---|---|
| | found | calc. |
| %C | 59.97 | 59.96 |
| %H | 12.11 | 12.08 |
| %N | 27.83 | 27.97 |

EXAMPLE B 1-methyl-2-(1-methylethyl)-hexahydropyrimidine

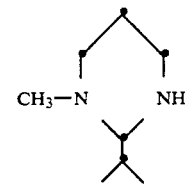

The compound is prepared in the manner described in U.S. Pat. No. 4,404,379.

Boiling point: 91° C./93 mbar $^1$H-NMR (CDCl$_3$): $\delta$3.02 (dm, J=12 Hz, 1 Heq); 2.88 (dm, J=12 Hz, 1 Heq); 2.54 (d, J=3 Hz, 1 H); 2.52 (td, Jgem=12 Hz, Jvic=3 Hz, 1 Hax); 2.25 (td, Jgem=12 Hz, Jvic=3 Hz, 1 Hax); 2.08 (s, 3H); 1.95 (m, 1 Hax); 1.61 (m, 1H); 1.38 (dm, J=12 Hz, 1 Heq); 0.95 (d, J=6.6 Hz, 3H); 0.88 (d, J=6.6 Hz, 3H).

$^{13}$C-NMR (CDCl$_3$): $\delta$83.1; 56.8; 45.8; 40.6; 28.4; 27.2; 19.6; 14.7.

| C$_8$H$_{18}$N$_2$ | Elemental analysis: | |
|---|---|---|
| | found | calc. |
| %C | 67.35 | 67.49 |

-continued

| Elemental analysis: C₈H₁₈N₂ | found | calc. |
|---|---|---|
| %H | 12.62 | 12.65 |
| %N | 19.66 | 19.68 |

EXAMPLE C 1-(2-hydroxyethyl)-3-(2-cyanoethyl)-hexahydropyrimidine

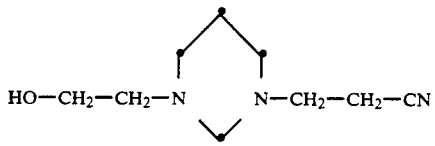

The compound is prepared in the manner described in EP-A 70536.
Boiling point: 81° C./0.13 mbar
$^1$H-NMR (CDCl$_3$): δ3.62 (t, J=5.3 Hz, C$\underline{H_2}$—OH); 3.32 (s, N—C$\underline{H_2}$—N); 2.82–2.43 (m, 10H); 1.68 (p, J=5.7 Hz, 2H).
$^{13}$C-NMR (CDCl$_3$): δ118.2; 74.4; 58.3; 55.9; 51.3; 51.2; 49.3; 22.2; 15.8.

| Elemental analysis: C₉H₁₇N₃O | found | calc. |
|---|---|---|
| %C | 59.01 | 58.99 |
| %H | 9.43 | 9.35 |
| %N | 22.72 | 22.93 |

EXAMPLE D 1-methyl-2-pentamethylene-hexahydropyrimidine

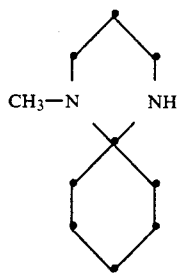

52.8 g (6 mol) of 3-methylaminopropylamine are added dropwise to a solution of 590 g (6 mol) of cyclohexanone in 400 ml of cyclohexane. The solution is then heated under reflux in a water separator, under a nitrogen atmosphere, until approximately 100 ml of water have been separated off (10 hours). The solvent is then removed under reduced pressure and the residue is subjected to fractional distillation. 680 g of 1-methyl-2-pentamethylene-hexahydropyrimidine are obtained.
Boiling point: 112° C./93 mbar
$^{13}$C-NMR (CDCl$_3$): δ69.2; 48.3; 38.5; 37.1; 29.7; 25.8; 25.4; 21.4.

| Elemental analysis: C₁₀H₂₀N₂ | found | calc. |
|---|---|---|
| %C | 71.45 | 71.42 |

-continued

| Elemental analysis: C₁₀H₂₀N₂ | found | calc. |
|---|---|---|
| %H | 11.91 | 11.98 |
| %N | 17.29 | 16.65 |

EXAMPLE E

1-[3-(trimethoxysilyl)propyl]-2-(1-methylethyl)-imidazolidine

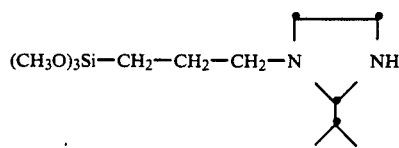

32.3 g (0.45 mol) of isobutyraldehyde are added dropwise to a solution of 100 g (0.45 mol) of 3-(2-aminoethylamino)propyltrimethoxysilane in 200 ml of dry cyclohexane. The solution is then heated under reflux in a water separator until 20 ml of water have been separated off (10 hours).
The solvent is then removed under reduced pressure and the residue is subjected to fractional distillation. 16 g of 1-[3-(trimethoxysilyl)propyl]-2-(1-methylethyl-)imidazolidine are obtained.
$^1$H-NMR (CDCl$_3$): δ3.24–2.85 (m, 4H); 3.57 (s, OC$\underline{H_3}$); 2.78–2.57 (m, N—C$\underline{H}$—N); 2.38–2.15 (m, C$\underline{H_2}$—N); 1.86–1.45 (m, 3H); 0.98 (d, J=7.4 Hz, C$\underline{H_3}$); 0.83 (d, J=7.4 Hz, C$\underline{H_3}$); 0.79–0.56 (m, C$\underline{H_2}$—Si).
$^{13}$C-NMR (CDCl$_3$): δ84.7; 56.5; 53.3; 50.2; 44.2; 29.9; 22.2; 19.5; 15.1; 6.6.

| Elemental analysis: C₁₂H₂₈N₂O₃Si | found | calc. |
|---|---|---|
| %C | 52.03 | 52.17 |
| %H | 10.12 | 10.14 |
| %N | 10.14 | 10.14 |

EXAMPLE F

1-[3-(trimethoxysilyl)propyl]-2-pentamethylene-imidazolidine

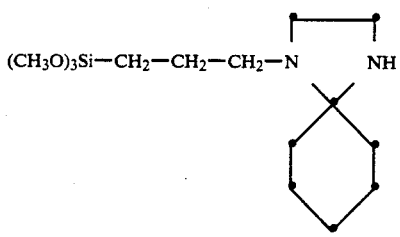

The procedure of Example E is followed, but 44.1 g (0.45 mol) of cyclohexanone are added dropwise and 18 ml of water are separated off (12 hours). 120 g of product are obtained[1].

[1] Approximately 10% of the open structure can be established by $^{13}$C-NMR (δ174.0) and $^1$H-NMR (δ3.43, OCH$_3$). The proportion of open structure is calculated by integration of the two methoxy peaks at 3.43 and 3.57 ppm. Tautomerism between two similar structures is mentioned by C. Chapuis et al., Bull. Soc. Chim. Fr. 1973, 977.

$^1$H-NMR (CDCl$_3$): δ3.57 (m, OC$\underline{H}$_3); 3.06-2.66 (m, 4H); 2.55-2.28 (m, 2H); 1.39-1.25 (m, 12H); 0.75-0.59 (m, C$\underline{H}_2$—Si).

$^{13}$C-NMR (CDCl$_3$): δ78.4; 51.6; 50.5; 50.2; 42.3; 31.3; 25.9; 23.5; 22.7; 6.5.

| Elemental analysis: | | |
|---|---|---|
| C$_{14}$H$_{30}$N$_2$O$_3$Si | found | calc. |
| %C | 55.85 | 55.54 |
| %H | 9.84 | 9.91 |
| %N | 10.14 | 9.26 |

EXAMPLE G

N-methyl-3-(2,2-dimethylpropylimino)-propylamine

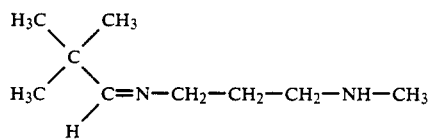

75.0 g (0.87 mol) of pivalaldehyde are added dropwise to a solution of 76.7 g (0.87 mol) of 3-methylaminopropylamine in 200 ml of dry cyclohexane. After the addition, the solution is heated under reflux in a water separator for 3 hours. The solvent is then removed in a rotary evaporator and the residue is distilled. Boiling point: 69° C./67 mbar $^1$H-NMR (CDCl$_3$): δ7.51 (t, J=1.1 Hz, C$\underline{H}$=N); 3.43 (td, J=6.8 Hz, J=1.1 Hz, C$\underline{H}_2$—N=C); 2.$\overline{59}$ (t, J=6.8 Hz, C$\underline{H}_2$—NH); 2.42 (s, N—C$\underline{H}_3$); 1.75 (p, J=6.8 Hz, 2H); 1.$\overline{06}$ (s, CH$_3$).

$^{13}$C-NMR ($\overline{C}$DCl$_3$): δ171.1; 59.0; 49.7; 36.1; 35.5; 30.6; 26.5.

| Elemental analysis: | | |
|---|---|---|
| C$_9$H$_{20}$N$_2$ | found | calc. |
| %C | 69.05 | 69.17 |
| %H | 12.96 | 12.90 |
| %N | 18.11 | 17.93 |

EXAMPLE H

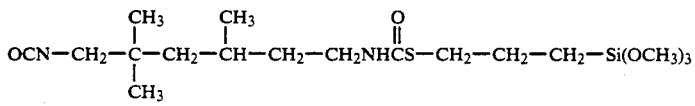

A mixture of 150 g (0.714 mol) of freshly distilled 1,6-diisocyanato-2,2,4-trimethylhexane and 140.2 g (0.714 mol) of 3-mercaptopropyltrimethoxysilane is heated at 140° C. for 2 hours under a nitrogen atmosphere. 275.2 g of the product are obtained in the form of a colourless liquid having the following analytical data:

Viscosity (according to Epprecht): η$_{25}$=380 mPa.s $^{13}$C-NMR (CDCl$_3$, selected signals): δ167.1 (br, N$\underline{C}$O—S); 122.2 (br, N$\underline{C}$O); 50.3 (O$\underline{C}$H$_3$); 8.6 (Si—$\underline{C}$H$_2$).

| Elemental analysis: | | |
|---|---|---|
| C$_{17}$H$_{34}$N$_2$O$_5$SSi | found | calc. |
| %C | 50.17 | 50.17 |
| %H | 8.45 | 8.36 |
| %N | 6.82 | 6.88 |

EXAMPLE 1

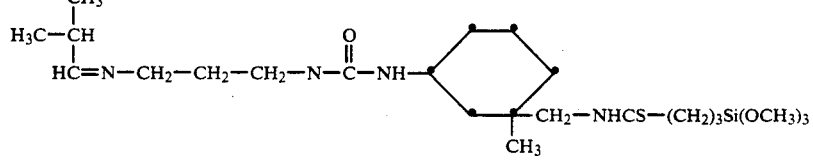

A mixture of 143.5 g (0.642 mol) of isophoronediisocyanate and 126.0 g (0.642 mol) of 3-mercaptopropyltrimethoxysilane is heated at 140° C. for 6 hours under a nitrogen atmosphere. The mixture is then allowed to cool to room temperature, and a solution of 90.8 g (0.642 mol) of 1-methyl-2-(1-methylethyl)-hexahydropyrimidine in 200 ml of dry toluene is added dropwise in such a manner that the temperature does not exceed 35° C. The mixture is then stirred at room temperature for a further 30 minutes and then the solvent is removed in a rotary evaporator at 100° C./0.1 mbar, yielding 351 g of product having the following analytical data:

Melting point: 40°-50° C.

$^1$H-NMR (CDCl$_3$, selected signals): δ7.55 (d, J=5 Hz, C$\underline{H}$=N); 6.02-5.08 (br, m, N—CO—N$\underline{H}$ +S—C$\overline{O}$—N$\underline{H}$); 3.56 (s, OC$\underline{H}_3$); 2.88 (s, N—C$\underline{H}_3$); 2.$\overline{41}$ (qd, J=10 Hz, 6 Hz, (CH$_3$)$_2$$\overline{C}$H).

$^{13}$C-NMR (CDCl$_3$, selected signals): 169.8 (C$\underline{H}$=N); 167.3 and 165.8 (N—$\underline{C}$O—S, two isomers); $\overline{1}$58.8 and 157.9 (N—$\underline{C}$O—N, two isomers); 56.6 ($\underline{C}$H$_2$—N=C); 50.0 (O—$\underline{C}$H$_3$); 45.7 ($\underline{C}$H$_2$N(CH$_3$)C$\overline{O}$—N); 33.5 (N—$\underline{C}$H$_3$); $\overline{18}$.4 ($\underline{C}$(CH$_3$)$_2$); $\overline{8}$.2 (Si—$\underline{C}$H$_2$).

| Elemental analysis: | | |
|---|---|---|
| C$_{28}$H$_{54}$N$_4$O$_5$SSi | found | calc. |
| %C | 55.57 | 55.58 |
| %H | 9.31 | 9.51 |
| %N | 9.75 | 9.97 |
| %S | 5.77 | 5.71 |

EXAMPLE 2

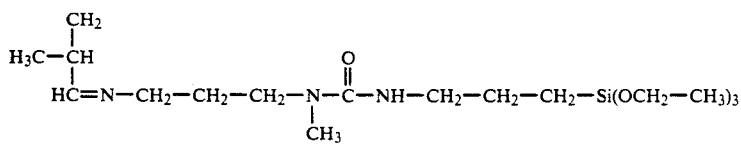

A solution of 34.4 g (0.14 mol) of isocyanatopropyl-triethoxysilane in 50 ml of dry toluene is added dropwise to a solution of 20.0 g (0.142 mol) of 1-methyl-2-(1-methylethyl)hexahydropyrimidine in 50 ml of dry toluene, the temperature being kept below 35° C. When the addition is complete, the mixture is stirred at room temperature for 7 hours. The solvent is then removed in a rotary evaporator at 100° C./0.1 mbar, yielding 50 g of a colourless liquid having the following analytical data:

$^1$H-NMR (CDCl$_3$): $\delta$7.58 (d, J=6 Hz, C$\underline{H}$=N); 5.91 (br.t, N—CO—N$\underline{H}$); 3.80 (q, J=7 Hz, OC$\underline{H_2}$); 3.25–3.02 (m, 6H); 2.88 (s, $\overline{N}$—C$\underline{H_3}$); 2.41 (qd, J=10 Hz, 6 Hz, (CH$_3$)$_2$C$\underline{H}$); 1.95–1.20 ($\overline{m}$, 4H); 1.13 (d, J=10 Hz, 6H); 1.05 (t, J=7 Hz, 9H); 0.80 (m, 2H).

$^{13}$C-NMR (CDCl$_3$): $\delta$169.3; 158.6; 57.7; 56.5; 45.6; 43.0; 33.4; 29.0; 23.3; 18.6; 17.7; 7.4.

Elemental analysis:

| C$_{18}$H$_{39}$N$_3$O$_4$S | found | calc. |
|---|---|---|
| %C | 55.55 | 55.49 |
| %H | 10.02 | 10.09 |
| %N | 10.74 | 10.79 |

EXAMPLE 3

$^1$H-NMR (CDCl$_3$, selected signals): $\delta$7.58 (d, J=6 Hz, C$\underline{H}$=N); 6.21–5.50 (br.m, N—CO—NH +S—CO—N$\underline{H}$); 3.56 (s, OC$\underline{H_3}$); 2.41 (qd, J=10 Hz, $\overline{6}$ Hz, (CH$_3$)$_2$C$\underline{H}$).

$^{13}$C-NMR (CDCl$_3$, selected signals): $\delta$169.6 (C$\underline{H}$=N); 167.1 (br, N—$\underline{C}$O—S); 158.5 (N—$\underline{C}$O—N); 56.5 ($\underline{C}$H$_2$—N=C); 50.1 (O$\underline{C}$H$_3$); 46.1 ($\underline{C}$H$_2$N(C$\underline{H_3}$)CO—N); 33.5 (N—$\underline{C}$H$_3$); 19.4 (C($\underline{C}$H$_3$)$_2$); 8.2 (Si—$\underline{C}$H$_2$).

Elemental analysis:

| C$_{25}$H$_{52}$N$_4$O$_5$SSi | found | calc. |
|---|---|---|
| %C | 54.23 | 54.66 |
| %H | 9.48 | 9.47 |
| %N | 9.93 | 10.20 |

EXAMPLE 4

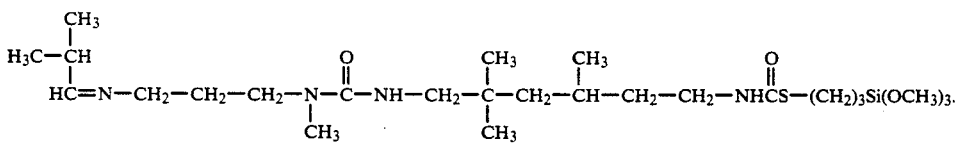

A mixture of 50 g (0.257 mol NCO) of partially trimerised hexamethylene-diisocyanate having an isocyanate content of 21.6% (the Bayer AG product Desmodur ® N 3200) and 33.7 g (0.171 mol) of 3-mercaptopropyltrimethoxysilane is heated at 140° C. for 60 minutes. The mixture is then allowed to cool to room temperature and a solution of 12.2 g (0.0857 mol) of 1-methyl-3-(1-methylethyl)-hexahydropyrimidine in 100 ml of dry toluene is added dropwise in such a manner that the temperature remains below 35° C. The mixture is then stirred at room temperature for 10 hours and then the solvent is removed in a rotary evaporator at 100° C./0.1 mbar. The product is obtained in the form of a viscous material having the following analytical data:

Viscosity (according to Epprecht): $\eta_{80}$=66,500 mPa.s $^1$H-NMR (CDCl$_3$, selected signals): $\delta$7.59 (d, J=6 Hz, C$\underline{H}$=N); 6.15–5.60 (br, N—CO—NH +S—CO—N$\underline{H}$); 3.57 (s, OC$\underline{H_3}$); 2.41 (qd, J=7 Hz, $\overline{6}$ Hz, (CH$_3$)$_2$C$\underline{H}$); 1.08 (d, J=7 Hz, C$\underline{H_3}$).

A mixture of 150 g (0.714 mol) of freshly distilled 1,6-diisocyanato-2,2,4-trimethylhexane and 140.2 g (0.714 mol) of 3-mercaptopropyltrimethoxysilane is heated at 140° C. for 2 hours under a nitrogen atmosphere, and then the mixture is allowed to cool to room temperature and a solution of 100.8 g (0.714 mol) of 1-methyl-2-(1-methylethyl)-hexahydropyrimidine in 200 ml of dry toluene is added dropwise in such a manner that the temperature is kept below 35° C. The mixture is then stirred at room temperature for a further 45 minutes and then the solvent is removed in a rotary evaporator at 100° C./-0.1 mbar, yielding 347 g of a viscous liquid having the following analytical data:

Viscosity (according to Epprecht): $\eta_{25}$=19,200 mPa.s $^{13}$C-NMR (CDCl$_3$, selected signals): δ170.1 (C̲H=N); 167.4 (N—C̲O—S); 159.4 (N—C̲—N); 156.6 (isocyanurate ring); 5̲6.9 (C̲H$_2$—N=C); 5̲0.4 (OC̲H$_3$); 46.1 (C̲H$_2$N(CH$_3$)CO—N̲); 34.0 (N—C̲H$_3$); 19.2 (C(C̲H$_3$)$_2$); 8.7 (Si—C̲H$_2$).

| Elemental analysis: C$_{44}$H$_{86}$N$_8$O$_{12}$S$_2$Si$_2$ | | |
|---|---|---|
| | found | calc. |
| %C | 51.60 | 50.84 |
| %H | 8.68 | 8.34 |
| %N | 11.40 | 10.78 |
| %S | 5.73 | 6.17 |

EXAMPLE 5

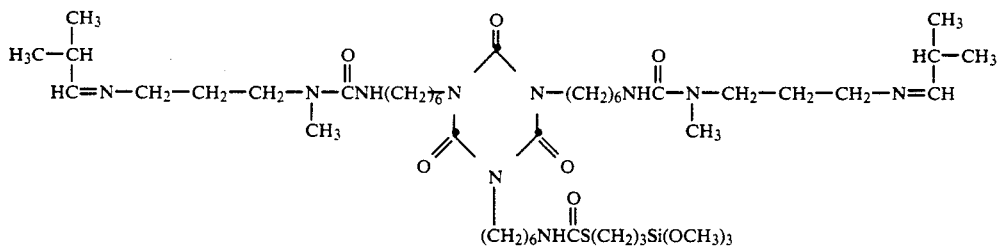

The procedure of Example 4 is followed. 50 g (0.257 mol NCO) of partially trimerised hexamethylene-diisocyanate having an isocyanate content of 21.6% (the Bayer AG product Desmodur® N 3200), 16.8 g (0.0857 mol) of 3-mercaptopropyltrimethoxysilane and 24.4 g (0.171 mol) of 1-methyl-2-(1-methylethyl)hexahydropyrimidine are reacted. There is obtained a viscous material having the following analytical data:

Viscosity (according to Epprecht): η$_{80}$=56,300 mPa.s $^1$H-NMR (CDCl$_3$, selected signals): δ7 7.59 (d, J=6 Hz, CH=N); 6.12-5.50 (br, N—CO—NH + S—CO—NH); 3.56 (s, OCH$_3$); 2.88 (s, N—CH$_3$); 2.4̲1 (qd, J=7 Hz, 6̲ Hz, (CH$_3$)$_2$CH̲); 1.08 (d, J=7 Hz, CH$_3$).

$^{13}$C-NMR (CDCl$_3$, selected signals): δ169.9 (C̲H=N); 167.2 (N—C̲O—S); 159.3 (N—C̲O—N); 1̲56.6 (isocyanurate ring); 56.9 (C̲H$_2$—N=C̲); 50.4 (OC̲H$_3$); 46.1 (C̲H$_2$N(CH$_3$)CO—N̲); 34.0 (N—C̲H$_3$); 19.2̲ (C(C̲H$_3$)$_2$); 8.7 (Si—C̲H$_2$).

| Elemental analysis: C$_{46}$H$_{88}$N$_{10}$O$_9$SSi | | |
|---|---|---|
| | found | calc. |
| % C | 56.21 | 56.07 |
| % H | 9.23 | 9.00 |
| % N | 14.78 | 14.21 |
| % S | 3.10 | 3.25 |

EXAMPLE 6

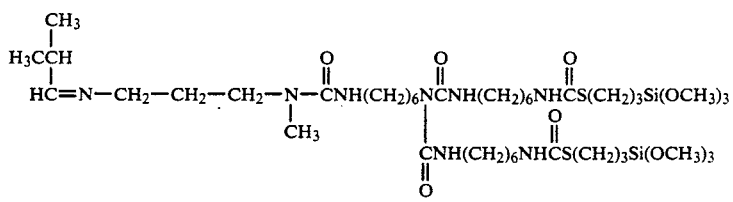

The procedure of Example 4 is followed. 50 g (0.255 mol NCO) of biuret-containing partially hydrolysed hexamethylene-diisocyanate having an isocyanate content of 21.3% (the Bayer AG product Desmodur® N 100), 33.5 g (0.17 mol) of 3-mercaptopropyltrimethoxysilane and 12 g (0.085 mol) of 1-methyl-2-(1-methylethyl)-hexahydropyrimidine are reacted. There is obtained a viscous product having the following analytical data:

Viscosity (according to Epprecht): η$_{40}$=88,320 mPa.s $^1$H-NMR (CDCl$_3$, selected signals): δ7.59 (d, J=6 Hz, CH=N); 6.20-5.60 (br, N—CO—NH + S—CO—NH); 3.57 (s, OCH$_3$); 2.89 (s, N—CH$_3$); 2.4̲1 (qd, J=7 Hz, 6̲ Hz, (CH$_3$)$_2$CH̲); 1.08 (d, J=7 Hz, CH$_3$).

| Elemental analysis: C$_{43}$H$_{97}$N$_8$O$_{11}$S$_2$Si$_2$ | | |
|---|---|---|
| | found | calc. |
| % C | 51.22 | 50.51 |
| % H | 8.76 | 9.56 |
| % N | 11.28 | 10.96 |
| % S | 5.59 | 6.27 |

EXAMPLE 7

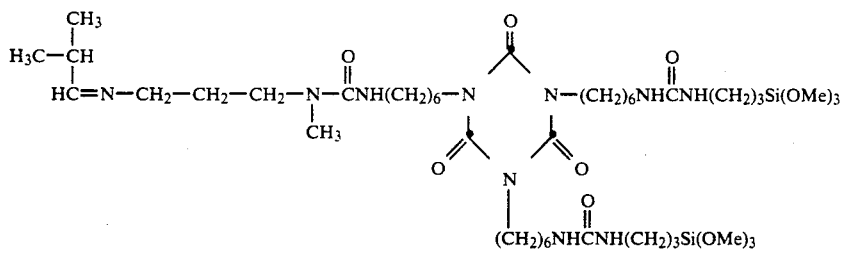

A solution of 50 g (0.257 mol) of partially trimerised hexamethylene-diisocyanate having an isocyanate content of 21.6% (the Bayer AG product Desmodur ® N 3200) in 50 ml of dry toluene is placed, under a nitrogen atmosphere, in a vessel equipped with a mechanical stirrer, a dropping funnel and a thermometer, and the vessel is immersed in an ice bath. A solution of 30.6 g (0.171 mol) of 3-aminopropyltrimethoxysilane in dry toluene is then added dropwise. An exothermic reaction begins immediately; the rate of dropwise addition is such that the temperature is kept below 30° C. When the addition is complete, the mixture is stirred at room temperature for one hour and then heated at 50° C. for one hour. The mixture is then allowed to cool to room temperature and a solution of 12.2 g (0.0857 mol) of 1-methyl-2-(1-methylethyl)-hexahydropyrimidine in 100 ml of dry toluene is added dropwise. When the addition is complete, the mixture is stirred at room temperature for one hour and then the solvent is removed in a rotary evaporator at 100° C./0.1 mbar, yielding a product having the following analytical data:

Viscosity (according to Epprecht): $\eta_{80}=39{,}040$ mPa.s $^1$H-NMR (CDCl$_3$, selected signals): $\delta$7.59 (d, J=6 Hz, C$\underline{H}$=N); 6.15–5.05 (br, N—CO—N$\underline{H}$); 3.57 (s, OC$\underline{H}_3$); 2.88 (s, N—C$\underline{H}_3$); 2.41 (qd, J=7 Hz, 6 Hz, (C$\overline{H}_3$)$_2$C$\underline{H}$); 1.08 (d, J=7 Hz, C$\underline{H}_3$).

| Elemental analysis: | | |
| $C_{44}H_{88}N_{10}O_{12}Si_2$ | found | calc. |
| --- | --- | --- |
| %C | 53.38 | 52.59 |
| %H | 9.05 | 8.76 |
| %N | 14.35 | 13.94 |

EXAMPLE 8

A mixture of 50 g (0.257 mol NCO) of partially trimerised hexamethylene-diisocyanate having an isocyanate content of 21.6% (the Bayer AG product Desmodur ® N 3200) and 16.8 g (0.0857 mol) of 3-mercaptopropyltrimethoxysilane is heated at 140° C. for 60 minutes and then allowed to cool to room temperature. A solution of 15.3 g (0.0857 mol) of 3-aminopropyltrimethoxysilane in 50 ml of dry toluene is then added dropwise in such a manner that the temperature is kept below 35° C. When the addition is complete, the mixture is stirred at room temperature for 2 hours. A solution of 12.2 g (0.0857 mol) of 1-methyl-2-(1-methylethyl)-hexahydropyrimidine in 100 ml of dry toluene is then added dropwise in such a manner that the temperature is kept below 35° C. When the addition is complete, the mixture is stirred at room temperature for 2 hours and then the solvent is removed in a rotary evaporator at 100° C./0.1 mbar, yielding a viscous product having the following analytical data:

Viscosity (according to Epprecht): $\eta_{80}=102{,}400$ mPa.s $^1$H-NMR (CDCl$_3$, selected signals): $\delta$7.59 (d, J=6 Hz, C$\underline{H}$=N); 6.20–5.05 (br, N—CO—N$\underline{H}$ +S—CO—N$\underline{H}$); 3.57 (s, OC$\underline{H}_3$); 2.88 (s, N—C$\underline{H}_3$); 2.$\overline{41}$ (qd, J=7 Hz, 6 Hz, (CH$_3$)$_2$C$\underline{H}$); 1.08 (d, J=7 Hz, C$\underline{H}_3$).

| Elemental analysis: $C_{44}H_{87}N_9O_{12}SSi_2$ | | |
| | found | calc. |
| --- | --- | --- |
| % C | 52.17 | 51.69 |
| % H | 8.75 | 8.58 |
| % N | 12.97 | 12.33 |
| % S | 2.93 | 3.14 |

EXAMPLE 9

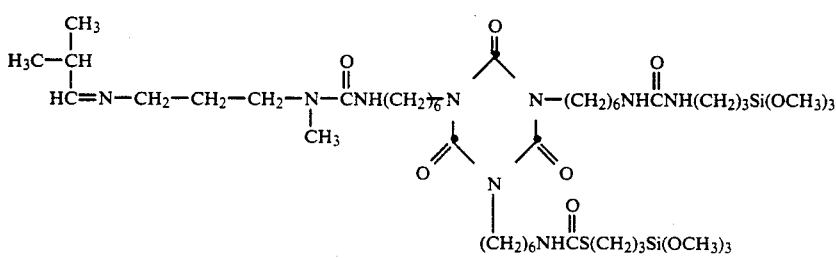

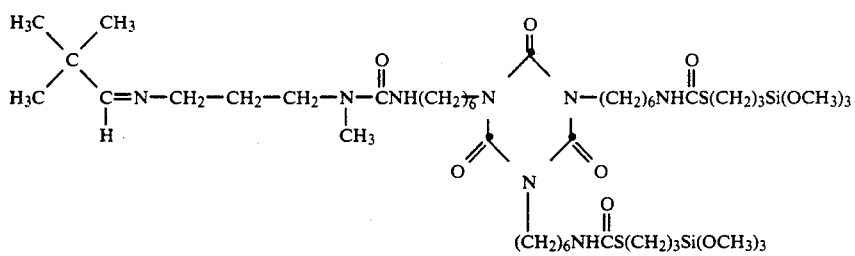

The procedure of Example 4 is followed. 200 g (1.028 mol NCO) of partially trimerised hexamethylenediisocyanate having an isocyanate content of 21.6% (the Bayer AG product Desmodur® N 3200), 134.8 g (0.684 mol) of 3-mercaptopropyltrimethoxysilane and 53.7 g (0.343 mol) of N-methyl-3-(2,2-dimethylpropylimino)-propylamine are reacted.

Viscosity (according to Epprecht): $\eta_{80}=6,080$ mPa.s $^1$H-NMR (CDCl$_3$, selected signals): $\delta$7.56 (br.s, C$\underline{H}$=N); 6.20–5.70 (br, N—CO—N$\underline{H}$+S—CO—N$\underline{H}$); 3.$\overline{56}$ (s, OC$\underline{H}_3$); 1.07 (s, C$\underline{H}_3$).

$^{13}$C-NMR (CDCl$_3$, selected signals): 172.0 ($\underline{C}$H=N); 166.7 (NH—$\underline{C}$O—S); 159.0 (N—$\underline{C}$O—NH); 156.0 (isocyanurate ring); 50.2 (O$\underline{C}$H$_3$); 35.9 ($\underline{C}$(CH$_3$)$_3$); 33.7 (N—$\underline{C}$H$_3$); 26.6 ($\underline{C}$H$_3$).

| Elemental analysis: C$_{45}$H$_{88}$N$_8$O$_{12}$S$_2$Si$_2$ | | |
|---|---|---|
| | found | calc. |
| %C | 51.85 | 51.30 |
| %H | 8.64 | 8.42 |
| %N | 11.48 | 10.64 |

EXAMPLE 10

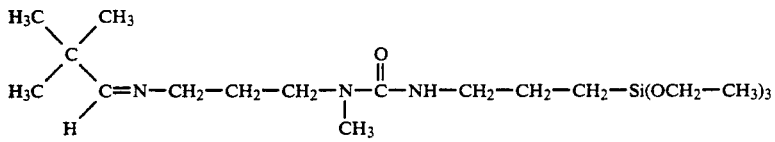

A solution of 23.8 g (0.096 mol) of isocyanatopropyltriethoxysilane in 30 ml of dry toluene is added dropwise to a solution of 15 g (0.096 mol) of N-methyl-3-(2,2-dimethylpropylimino)-propylamine in 20 ml of dry toluene, and the mixture is stirred at room temperature for one hour. The solvent is then removed in a rotary evaporator at 90° C./−0.1 mbar, yielding 35.7 g of a colourless liquid having the following analytical data:

Viscosity (according to Epprecht): $\eta_{25}=120$ mPa.s $^1$H-NMR (CDCl$_3$): $\delta$7.52 (br.s, C$\underline{H}$=N); 6.03 (br, N—CO—N$\underline{H}$); 3.39–3.05 (m, 8H); 3.77 (q, J=7.0 Hz, OC$\underline{H}_2$); 2.85 (s, C$\underline{H}_3$—N); 1.79–1.48 (m, 2H); 1.18 (t, J=7.0 Hz, OCH$_2$C$\underline{H}_3$); 1.04 (s, C$\underline{H}_3$); 0.66–0.99 (m, C$\underline{H}_2$—Si).

$^{13}$C-NMR (CDCl$_3$): $\delta$171.8; 158.8; 57.9; 56.3; 45.4; 43.2; 35.8; 33.5; 29.3; 26.5; 23.6; 18.0; 7.4.

| Elemental analysis: C$_{19}$H$_{41}$N$_3$O$_4$Si | | |
|---|---|---|
| | found | calc. |
| %C | 56.14 | 56.57 |
| %H | 10.09 | 10.17 |
| %N | 10.33 | 10.42 |

EXAMPLE 11

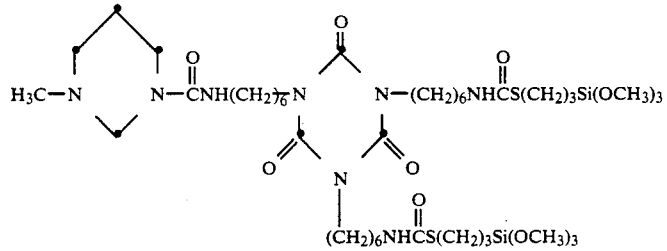

The procedure of Example 4 is followed. 50 g (0.257 mol NCO) of partially trimerised hexamethylenediisocyanate having an isocyanate content of 21.6% (the Bayer AG product Desmodur® N 3200), 33.7 g (0.171 mol) of 3-mercaptopropyltrimethoxysilane and 8.6 g (0.0857 mol) of 1-methylhexahydropyrimidine are reacted. There is obtained a product having the following analytical data:

Viscosity (according to Epprecht): $\eta_{80}=28,160$ mPa.s $^1$H-NMR (CDCl$_3$, selected signals): $\delta$6.15–5.70 (br, S—CO—N$\underline{H}$); 5.20–4.90 (br, N—CO—N$\underline{H}$); 3.90 (s, N—CH$_2$—$\overline{N}$); 3.56 (s, OC$\underline{H}_3$); 2.26 (s, N—C$\underline{H}_3$).

$^{13}$C-NMR (CDCl$_3$, selected signals): $\delta$167.1 (NH—$\underline{C}$O—S); 157.5 (N—$\underline{C}$O—N); 156.4 (isocyanurate ring); 67.8 (N—$\underline{C}$H$_2$—N); 50.4 (O$\underline{C}$H$_3$); 42.0 (N—$\underline{C}$H$_3$); 8.5 ($\underline{C}$H$_2$—Si).

| Elemental analysis: C$_{41}$H$_{80}$N$_8$O$_{12}$S$_2$Si$_2$ | | |
|---|---|---|
| | found | calc. |
| %C | 50.58 | 49.37 |
| %H | 8.50 | 8.08 |

-continued

| Elemental analysis: $C_{41}H_{80}N_8O_{12}S_2Si_2$ | | |
|---|---|---|
| | found | calc. |
| % N | 12.15 | 11.23 |
| % S | 5.93 | 6.43 |

EXAMPLE 12

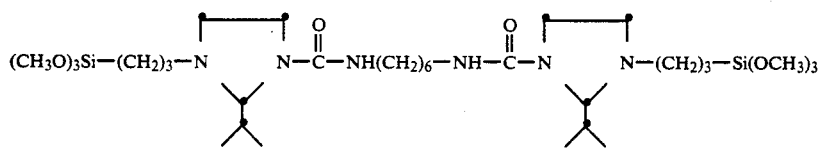

A solution of 3 g (0.018 mol) of hexamethylenediisocyanate in 50 ml of dry toluene is added dropwise, with stirring, to a solution of 10 g (0.036 mol) of 1-[3-(trimethoxysilyl)propyl]-2-(1-methylethyl)-imidazolidine in 50 ml of dry toluene. The mixture is then stirred for a further 2 hours and then the solvent is removed in a rotary evaporator at 90° C./0.1 mbar, yielding 13 g of a viscous material having the above structure[2] and the following analytical data:

[2]Approximately 15% of the open structure can be established by $^1$H-NMR.

Viscosity (according to Epprecht): $\eta_{25} = 80,250$ mPa.s $^1$H-NMR (CDCl$_3$, selected signals): $\delta 4.39$ (br.t, N—CO—N$\underline{H}$); 4.27 (d, J=6.4 Hz, N—C$\underline{H}$—N); 3.56 (s, OC$\underline{H}_3$); 0.74–0.55 (m, C$\underline{H}_2$—Si).

| Elemental analysis: $C_{32}H_{68}N_6O_8Si_2$ | | |
|---|---|---|
| | found | calc. |
| % C | 53.07 | 53.30 |
| % H | 9.43 | 9.51 |
| % N | 11.65 | 11.65 |

EXAMPLE 13

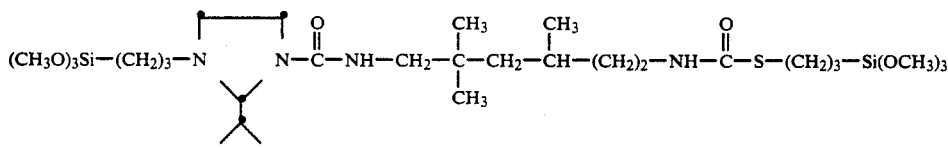

A solution of 5 g (0.018 mol) of 1-[3-(trimethoxysilyl)propyl]-2-(1-methylethyl)imidazolidine in 50 ml of dry toluene is added dropwise, with stirring, to a solution of 8.1 g (0.018 mol) of the product of Example H in 50 ml of dry toluene. The mixture is then stirred at room temperature for a further 24 hours and then the solvent is removed in a rotary evaporator at 95° C./0.1 mbar, yielding 13 g of a product having the above structure[3] and the following analytical data:

[3]Approximately 15% of the open structure can be established by $^1$H-NMR (analogously to Example 12).

Viscosity (according to Epprecht): $\eta_{25} = 68,200$ mPa.s $^1$H-NMR (CDCl$_3$, selected signals): $\delta 4.50$ (br, N—CO—N$\underline{H}$); 6.15 (br, N$\underline{H}$—CO—S); 4.27 (d, J=6.4 Hz, N—C$\underline{H}$—N); 3.56 (s, OC$\underline{H}_3$).

| Elemental analysis: $C_{29}H_{62}N_4O_8SSi_2$ | | |
|---|---|---|
| | found | calc. |
| % C | 50.78 | 50.95 |
| % H | 9.13 | 9.08 |
| % N | 8.15 | 8.19 |
| % S | 4.19 | 4.70 |

EXAMPLE 14

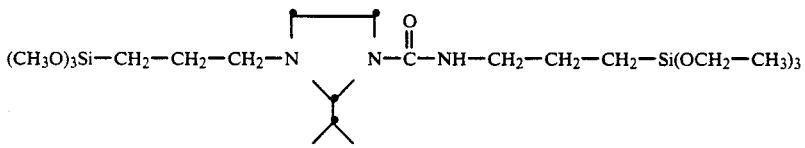

A solution of 15.0 g (0.054 mol) of 1-[3-(trimethoxysilyl)propyl]-2-(1-methylethyl)imidazolidine in 30 ml of dry toluene is added, with stirring, to a solution of 13.4 g (0.054 mol) of isocyanatopropyltriethoxysilane in 30 ml of dry toluene, and the mixture is then stirred at room temperature for a further 3 hours. The solvent is then removed in a rotary evaporator at 95° C./0.1 mbar, yielding 27 g of a product having the above structure[4] and the following analytical data:

[4]20% of the open structure can be established by $^1$H-NMR (analogously to Example 12).

Viscosity (according to Epprecht): $\eta_{25} = 1,952$ mPa.s $^1$H-NMR (CDCl$_3$): $\delta 4.47$ (br, N—CO—N$\underline{H}$); 4.27 (d, J=6.4 Hz, N—C$\underline{H}$—N); 3.81 (q, J=7.0 Hz, OC$\underline{H}_2$); 3.56 (s, OC$\underline{H}_3$); 3.34–2.82 (m, 8H); 2.54–2.15 (m, 2H); 1.91–1.56 (m, 3H); 1.22 (t, J=7.0 Hz, OCH$_2$—C$\underline{H}_3$); 1.02–0.89 (m, C(C$\underline{H}_3$)); 0.71–0.55 (m, C$\underline{H}_2$—Si).

$^{13}$C-NMR (CDCl$_3$): $\delta 156.9$; 84.2; 57.9; 57.7; 51.4; 50.0; 44.0; 42.7; 32.5; 23.2; 22.2; 18.5; 17.8; 7.2; 6.8.

| Elemental analysis: $C_{22}H_{49}N_3O_7Si_2$ | | |
|---|---|---|
| | found | calc. |
| % C | 50.97 | 50.45 |
| % H | 9.31 | 9.43 |
| % N | 8.87 | 8.02 |

EXAMPLE 15

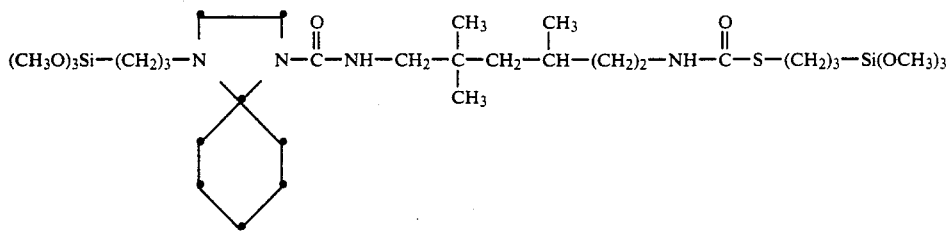

A solution of 13 g (0.044 mol) of 1-[3-(trimethoxysilyl)-propyl]-2-pentamethyleneimidazolidine in 100 ml of dry toluene is added dropwise, with stirring, to a solution of 20 g (0.044 mol) of the product of Example H in 100 ml of dry toluene. The mixture is then stirred at room temperature for a further 2 hours and then the solvent is removed in a rotary evaporator at 95° C./0.1 mbar, yielding a product having the above structure[5] and the following analytical data:

[5] The open structure can also be established (analogously to Example 12).

Viscosity (according to Epprecht): $\eta_{25} = 76,800$ mPa.s

| Elemental analysis: $C_{31}H_{65}N_4O_8SSi$ | | |
|---|---|---|
| | found | calc. |
| % C | 52.43 | 52.49 |
| % H | 9.23 | 8.97 |
| % N | 7.89 | 8.04 |
| % S | 4.51 | 4.72 |

EXAMPLE 16

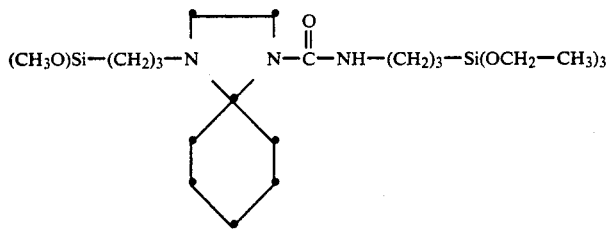

A solution of 15 g (0.049 mol) of 1-[3-(trimethoxysilyl)propyl]-2-pentamethylene-imidazolidine in 30 ml of dry toluene is added dropwise, with stirring, to a solution of 12.3 g (0.049 mol) of isocyanatopropyltriethoxysilane in 30 ml of dry toluene. The mixture is then stirred at room temperature for a further 3 hours and then the solvent is removed in a rotary evaporator at 95° C./0.1 mbar, yielding 27 g of a product having the above structure[6] and the following analytical data:

[6] The open structure can also be established (analogously to Example 12).

Viscosity (according to Epprecht): $\eta_{25} = 2,400$ mPa.s

| Elemental analysis: $C_{24}H_{51}N_3O_7Si_2$ | | |
|---|---|---|
| | found | calc. |
| % C | 51.65 | 52.43 |
| % H | 8.89 | 9.35 |
| % N | 8.32 | 7.64 |

EXAMPLE 17

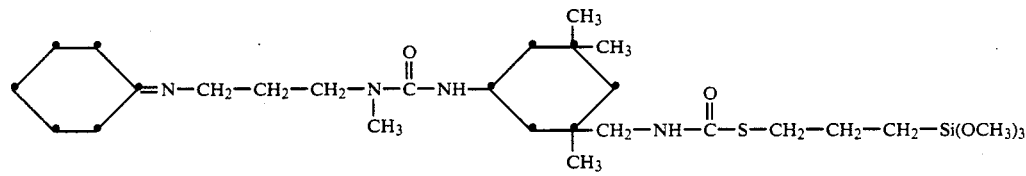

A mixture of 72.4 g (0.326 mol) of isophoronediisocyanate and 64.0 g (0.326 mol) of 3-mercaptopropyltrimethoxysilane is heated at 140° C. for 60 minutes, then it is allowed to cool to room temperature and then a solution of 54.8 g (0.326 mol) of 1-methyl-2-pentamethylene-hexahydropyrimidine is slowly added in such a manner that the temperature is kept below 35° C. The mixture is stirred for a further 30 minutes, and then the solvent is removed in a rotary evaporator at 100° C./0.1 mbar, yielding 188.6 g of a product having the following analytical data:

Melting point: 40° C.

| Elemental analysis: $C_{28}H_{54}N_4O_5SSi$ | | |
|---|---|---|
| | found | calc. |
| % C | 56.79 | 57.30 |
| % H | 9.54 | 9.27 |
| % N | 9.91 | 9.55 |
| % S | 5.48 | 5.46 |

EXAMPLE 18

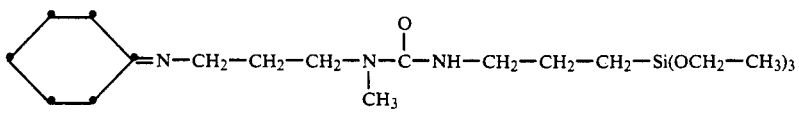

A solution of 28.7 g (0.116 mol) of isocyanatopropyl-triethoxysilane in 50 ml of dry toluene is added dropwise to a solution of 20.0 g (0.119 mol) of 1-methyl-2-pentamethylene-hexahydropyrimidine in 50 ml of dry toluene in such a manner that the temperature is kept below 35° C. When the addition is complete, the mixture is stirred at room temperature for 7 hours and then the solvent is removed in a rotary evaporator at 100° C./0.1 mbar, yielding 46.8 g of a yellow liquid having the following analytical data:

Viscosity (according to Epprecht): $\eta_{25}=80$ mPa.s

13C-NMR (CDCl3): δ172.9; 158.7; 57.9; 45.5; 44.9; 43.1; 39.5; 33.6; 28.9; 28.3; 27.3; 26.5; 25.6; 23.4; 17.8; 7.6.

| Elemental analysis: $C_{20}H_{41}N_3O_4Si$ | | |
|---|---|---|
| | found | calc. |
| % C | 57.54 | 57.79 |
| % H | 9.86 | 9.94 |
| % N | 10.59 | 10.11 |

EXAMPLE 19

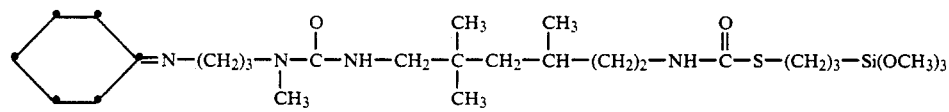

A mixture of 150 g (0.714 mol) of freshly distilled 1,6-diisocyanato-2,2,4-trimethylhexane and 140 g (0.714 mol) of 3-mercaptopropyltrimethoxysilane is heated at 140° C. for 2 hours under a nitrogen atmosphere and is then allowed to cool to room temperature. A solution of 120 g (0.714 mol) of 1-methyl-2-pentamethylene-hexahydropyrimidine in 200 ml of dry toluene is then added dropwise in such a manner that the temperature is kept below 35° C. When the addition is complete, the mixture is stirred at room temperature for a further 45 minutes and then the solvent is removed in a rotary evaporator at 100° C./0.1 mbar, yielding 380 g of a product having the following analytical data:

Melting point: 35° C.

| Elemental analysis: $C_{27}H_{54}N_4O_5SSi$ | | |
|---|---|---|
| | found | calc. |
| % C | 57.27 | 56.36 |
| % H | 9.64 | 9.36 |
| % N | 9.95 | 9.74 |
| % S | 3.12 | 3.35 |

EXAMPLE 20

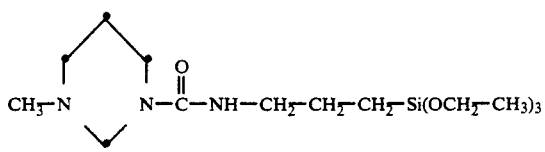

A solution of 24.7 g (0.0998 mol) of isocyanatopropyltriethoxysilane in 30 ml of dry toluene is added dropwise to a solution of 10.0 g (0.0998 mol) of 1-methylhexahydropyrimidine in 30 ml of dry toluene, and the mixture is then stirred at room temperature for 2 hours. The solvent is then removed in a rotary evaporator at 90° C./0.1 mbar, yielding 24.2 g of a colourless liquid having the following analytical data:

Viscosity (according to Epprecht): $\eta_{25}=400$ mPa.s

1H-NMR (CDCl3): δ4.94 (br.t, N—CO—NH); 3.90 (s, N—CH2—N); 3.81 (q, J=7.0 Hz, OCH2); 3.36 (t, J=5.8 Hz, 2H); 3.31-3.13 (m, 4H); 2.59 (t, J=5.8 Hz); 2.26 (s, N—CH3); 1.64 (p, J=5.8 Hz, 2H); 1.22 (t, J=7.0 Hz, CH3); 0.63 (t, J=7.2 Hz, CH2—Si).

13C-NMR (CDCl3): δ157.0; 67.3; 57.7; 54.2; 43.2; 43.0; 41.4; 23.3; 23.0; 17.7; 7.2.

| Elemental analysis: $C_{15}H_{33}N_3O_4Si$ | | |
|---|---|---|
| | found | calc. |
| % C | 51.67 | 51.84 |
| % H | 9.52 | 9.57 |
| % N | 11.72 | 12.09 |

EXAMPLE 21

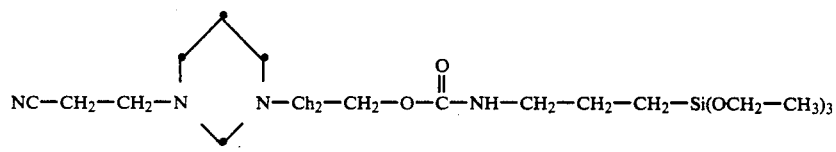

A solution of 4.86 g (0.0196 mol) of isocyanatopropyltriethoxysilane in 30 ml of dry toluene is added dropwise to a solution of 3.6 g (0.0196 mol) of 1-(2-hydroxyethyl)-3-(2-cyanoethyl)-hexahydropyrimidine in 30 ml of dry toluene at 100° C., and the mixture is then stirred at 100° C. for 1.5 hours. The solvent is then removed in a rotary evaporator at 90° C./0.1 mbar, yielding 8.2 g of a colourless liquid having the following analytical data:

Viscosity (according to Epprecht): $\eta_{25}=440$ mPa.s

¹H-NMR (CDCl₃): δ5.23 (br.t, N—CO—N$\underline{H}$); 4.15 (t, J=5.8 Hz, C$\underline{H}_2$—O—CO—NH); 3.81 (q, J=7.0 Hz, OC$\underline{H}_2$); 3.32 (s, N—C$\underline{H}_2$—N); 3.31-3.11 (m, 4H); 2.82-2.42 (m, 10H); 1.68-1.45 (m, 2H); 1.22 (d, J=7.0 Hz, C$\underline{H}_3$); 0.61 (t, J=7.2 Hz, C$\underline{H}_2$—Si).

¹³C-NMR (CDCl₃): δ155.8; 118.4; 74.4; 61.6; 57.7; 53.0; 51.9; 51.4; 49.4; 42.9; 22.8; 22.0; 17.8; 16.1; 7.1.

| Elemental analysis: C₁₉H₃₈N₄O₅Si | | |
|---|---|---|
|  | found | calc. |
| % C | 53.18 | 53.00 |
| % H | 8.98 | 8.90 |
| % N | 13.00 | 13.01 |

EXAMPLE 22

NC—CH₂—CH₂—N⟨⟩N—CH₂—CH₂—O—C(O)NH(CH₂)₆N⟨isocyanurate ring with two N—(CH₂)₆NHC(S)(CH₂)₃Si(OCH₃)₃ groups⟩

A mixture of 15.9 g (0.08 mol NCO) of partially trimerised hexamethylene-diisocyanate having an isocyanate content of 21.6% (the Bayer AG product Desmodur ® N 3200) and 10.7 g (0.054 mol) of 3-mercaptopropyltrimethoxysilane is heated at 140° C. for 60 minutes. The mixture is then allowed to cool to 100° C., and then 5.0 g of 1-(2-hydroxyethyl)-3-(2-cyanoethyl)-hexahydropyrimidine are added dropwise and the mixture is stirred at the same temperature for 5 hours. The solvent is then removed in a rotary evaporator at 95° C./0.1 mbar, yielding a product having the following analytical data:

Viscosity (according to Epprecht): $\eta_{80}$=7,680 mPa.s

¹H-NMR (CDCl₃, selected signals): δ6.10-5.60 (br, S—CO—N$\underline{H}$); 5.20-4.90 (br, O—CO—N$\underline{H}$); 4.15 (t, J=5.8 Hz, C$\underline{H}_2$—O—CO—N); 3.56 (s, OC$\underline{H}_3$); 3.32 (s, N—C$\underline{H}_2$—N).

¹³C-NMR (CDCl₃, selected signals): δ168.8 (N—CO—S); 156.3 (O—CO—NH); 156.1 (isocyanurate ring); 118.7 (CN); 74.7 (N—$\underline{C}$H₂—N); 62.1 ($\underline{C}$H₂—O—CO—NH); 50.2 (O$\underline{C}$H₃); 16.3 ($\underline{C}$H₂—CN); 8.3 ($\underline{C}$H₂—Si).

| Elemental analysis: C₄₅H₈₅N₉O₁₃S₂Si | | |
|---|---|---|
|  | found | calc. |
| % C | 51.09 | 50.02 |
| % H | 8.26 | 7.93 |
| % N | 12.55 | 11.67 |
| % S | 5.56 | 5.93 |

EXAMPLE 23

A) Prepolymer synthesis:

An isocyanate-terminated prepolymer is prepared by adding a mixture of 531 g of dry bishydroxy-terminated polypropylene glycol having a molecular weight of 2000 (the Bayer AG product Desmophen ® 1900U) and 0.3 ml of dibutyltin dilaurate to 150 g of methylenediphenyl-diisocyanate (the Upjohn product Isonate ® M125) at 80° C., within a period of one hour. 2.7 g of trimethylolpropane are then added, and the mixture is stirred at 80° C. for a further 2 hours until an isocyanate-terminated prepolymer having an isocyanate content of 2.4% has formed.

B) Adhesion to glass

5% dry pyrogenic silica (Aerosil 380) and 5% adhesion promoter according to Table 1 are added to the prepolymer obtained under A. A 5 mm thick polyurethane layer is then poured onto a glass plate. After two weeks' storage in air, the samples are stored in water at room temperature for two weeks. The results are shown in Table 1, where (– –) means that the layer can be removed easily and the glass surface remains clean; (–) means that the layer can be removed with difficulty and the glass surface remains clean; (+/–) means that most of the layer on the glass surface can be removed by scratching with a knife; (+) means that most of the layer remains adhered to the glass surface despite being scratched with a knife; (++) means that the whole of the layer remains adhered to the glass surface despite being scratched with a knife.

TABLE 1

| Adhesion promoter according to Example | Adhesion to glass |
|---|---|
| no adhesion promoter | — |
| 1 | ++ |
| 2 | ++ |
| 4 | ++ |
| 5ᵃ | ++ |
| 6 | ++ |
| 8 | ++ |
| 9 | ++ |
| 10 | ++ |
| 12 | + |
| 13 | ++ |
| 14 | + |
| 15 | + |
| 17 | + |
| 18 | + |

ᵃ10% adhesion promoter used

What is claimed is:

1. A compound of the formula I $$\left[ E-R^1-N(R^2)-(A)_p-\overset{Y}{\underset{\|}{C}}-NH- \right]_m T \quad\quad I$$

wherein

R¹ is C₂-C₃alkylene,

R² is hydrogen, unsubstituted C₁-C₆alkyl or C₁-C₆alkyl substituted by —OH, —CN or by —Si(OR³)₃₋qR⁴q, or C₂-C₆alkenyl, R³ is C₁-C₄alkyl, or two radicals R³ together are C₁-C₄alkylene, R⁴ is C₁-C₄alkyl or phenyl, and q is from 0 to 2, and
E is a radical of the formula

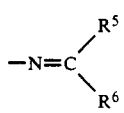

wherein
   $R^5$ is hydrogen or $C_1$-$C_4$alkyl and
   $R^6$ is hydrogen, or
   $R^5$ and $R^6$ together are $C_4$-$C_8$alkylene, or
   $R^9$ is $C_1$-$C_8$alkylene, and
   A is [—$(CH_2)_r$—O—], wherein r is 1, 2 or 3, and p is 0 or 1, and
   Y is oxygen or sulfur, and
wherein
   T is a radical —$R^9$—$Si(OR^3)_{3-q}R^4_q$, a radical of the formula

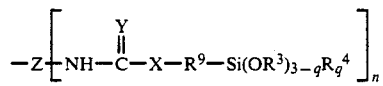

wherein $R^3$, $R^4$, $R^9$, Y and q are as defined above,
   X is —S— or —NH—, and
   Z is an organic radical derived from a polyisocyanate or polyisothiocyanate having at least two NCO or NCS groups respectively.
and
   m is 1 to 49
   n is 1 to 49.

2. A compound according to claim 1 of formula I wherein $R^1$ is ethylene.

3. A compound according to claim 1 wherein Y is O.

4. A compound according to claim 1 of formula I, wherein Z is derived from an aliphatic, cycloaliphatic, aliphatic/aromatic polyisocyanate or polyisothiocyanate having at least 2 NCO or NCS groups, this radical optionally containing one or more ester, ether, urethane, thiourethane, isocyanurate, urea or biuret functions.

5. A compound according to claim 4 of formula I, wherein Z is derived from an aliphatic or mixed aliphatic/aromatic polyisocyanate having at least 2 NCO groups, this radical Z optionally containing one or two ester, ether, urethane, thiourethane, isocyanurate, urea or biuret functions.

6. A compound according to claim 1 of formula I, wherein the radical Z has a mean molecular weight $M_n < 10,000$.

7. A compound according to claim 1 of formula I, wherein n and m each independently of the other are from 1 to 49.

8. A compound according to claim 1 of formula I, wherein the sum of n+m is from 2 to 50.

9. A compound according to claim 1 of formula I, wherein n is 1, 2 or 3 and m is 3, 2 or 1.

10. A compound according to claim 1 of formula I, wherein p is 0.

11. A compound according to claim 1 of formula I, wherein q is 0.

12. A compound according to claim 1 of formula I, wherein E is a radical of the formula

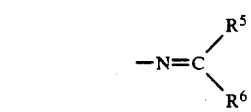

13. A compound according to claim 12 of formula I, wherein $R^5$ is isopropyl or tert.-butyl or $R^5$ together with $R^6$ is tetramethylene or pentamethylene.

14. A compound according to claim 1 of formula I, wherein T is a radical of the formula —$R^9$—$Si(OR^3)_{3-q}R^4_q$ or

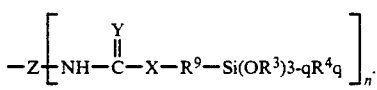

15. A compound according to claim 14 of formula I, wherein at least one radical X is —S—.

16. A compound according to claim 1 of formula I, wherein p is 0 and m is 1, E is a radical

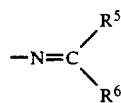

wherein $R^5$ is $C_3$— or $C_4$-alkyl and $R^2$ is $C_1$-$C_4$alkyl.

* * * * *